United States Patent [19]

Olson

[11] Patent Number: 4,692,140
[45] Date of Patent: Sep. 8, 1987

[54] LAVAGE/SUCTION TIP WITH DUAL SPLASH SHIELD

[75] Inventor: Daniel H. Olson, Louisville, Ohio

[73] Assignee: Snyder Laboratories, Inc., Dover, Ohio

[21] Appl. No.: 750,613

[22] Filed: Jul. 1, 1985

[51] Int. Cl.⁴ .............................................. A61M 7/00
[52] U.S. Cl. ..................................... 604/40; 604/35; 604/119
[58] Field of Search ................. 604/27, 35, 39–45, 604/73–76, 93, 146, 119, 147, 176, 264, 275, 276, 278, 279, 313, 902, 8, 9, 105–109, 177, 178, 168, 355; 128/361

[56] References Cited

U.S. PATENT DOCUMENTS

| | | | |
|---|---|---|---|
| D. 216,235 | 12/1969 | Slee et al. | D83/12 |
| 526,353 | 9/1894 | Lamb et al. | 604/39 |
| 724,913 | 4/1903 | Montgomery | 604/278 |
| 1,178,898 | 4/1916 | Young | |
| 1,602,215 | 4/1926 | Smith | |
| 1,889,425 | 3/1931 | Sorensen | |
| 2,065,779 | 12/1936 | Williams | 604/178 |
| 2,771,072 | 11/1956 | DeMontauge | 128/241 |
| 3,109,426 | 11/1963 | Noonan et al. | 128/240 |
| 3,202,152 | 8/1965 | Wood et al. | 128/361 |
| 3,469,571 | 9/1969 | Vass | 604/176 |
| 3,581,732 | 6/1971 | Ruiz | 604/278 |
| 3,690,323 | 9/1972 | Wortman et al. | 604/8 |
| 3,749,090 | 7/1973 | Stewart | 128/240 |
| 3,912,168 | 10/1975 | Mullins et al. | 239/102 |
| 4,089,337 | 5/1978 | Kronner | 604/178 |
| 4,215,476 | 8/1980 | Armstrong | 433/80 |
| 4,294,251 | 10/1981 | Greenwald et al. | 128/276 |
| 4,299,221 | 11/1981 | Phillips et al. | 128/276 |
| 4,301,798 | 11/1981 | Anderson | 128/239 |
| 4,340,365 | 7/1982 | Pisanu | 433/80 |
| 4,400,168 | 8/1983 | Buechel et al. | |
| 4,465,479 | 8/1984 | Meisch | 604/251 |
| 4,466,435 | 8/1984 | Murray | |
| 4,487,600 | 12/1984 | Brownlie et al. | 604/35 |
| 4,573,975 | 3/1986 | Frist et al. | 604/192 |

FOREIGN PATENT DOCUMENTS 1586089 3/1981 United Kingdom .
1602277 11/1981 United Kingdom .

OTHER PUBLICATIONS

American Cystoscope Makers Incorporated-advertisement catalogue, "Empyema Drain", (1952), p. 200.
Stryker Tips and Splash Shields ad-Stryker Corporation-Copyright, Sep. 1976.
Stryker OrthoLav advertisement-Stryker Corporation—no date available.
Micro-Aire ® Pulse Lavage-advertisement-Micro-Aire ® Surgical Instruments, Inc.-Copyright Micro-Aire Surgical Ins., 1984.
Pulsavac ™ Pulsatile Lavage Debridement System-Zimmer Brochure 83-010-5150-0243/15M ©, 1983, Snyder Laboratories, Inc.

Primary Examiner—Dalton L. Truluck
Assistant Examiner—Mario Costantino
Attorney, Agent, or Firm—Margaret L. Geringer

[57] ABSTRACT

A lavage/suction tip comprising an elongated barrel with a first pliable conical shield extending outwardly from the distal tip of the barrel and a second substantially rigid conical shield which is slidable upon the barrel. The lavage/suction tip is utilized to provide irrigating fluid to a surgical site while providing suction to remove fluids and debris away from the surgical site. The first shield helps to eliminate splashback of the fluid. The second shield may be positioned to surround the first shield to provide firm support about the first shield, yet with a flexible, pliable tip perimeter. Alternatively, the second shield may be secured on the tip spaced away from the first shield so that the pliable first shield is used alone and may be easily, manually formed to more closely match the tip of the first shield to the working area or surface of the surgical site.

17 Claims, 3 Drawing Figures

LAVAGE/SUCTION TIP WITH DUAL SPLASH SHIELD

BACKGROUND OF THE INVENTION

This invention generally relates to a lavage/suction tip for supplying and irrigating fluid to, and withdrawing by suction, unwanted fluid and debris from a surgical operating site. More particularly, this invention relates to the use of a shielding means to eliminate splashback of fluid from the surgical site.

Handheld lavage/suction devices have long been used in surgical and dental procedures for various purposes at the operating site or wound to facilitate the cleaning and irrigation of the wound or site. When such devices are used to direct fluid toward a surface such as a bone surface (i.e. an acetabular surface or a tibial plateau surface during joint replacement surgery) the debriding action needed to clean the surface creates a splashback of the fluid. This splashback is undesirable as it is messy and results in fluid splashing back on the operator of the lavage/suction device as well as on the floor and elsewhere. Such splashback could also result in a tendency for cross contamination problems.

Splash shields, such as a flat, substantially rigid, round planar disc shield, have been utilized with lavage/suction devices. This separate flat disc includes a centrally located hole therethrough enabling the single disc to be fitted about the distal end of a tubular lavage tip or nozzle. This type of shield, while preventing the fluid from splashing back on the user, does not contain the fluid in any way, and therefore fluid may still splash elsewhere about the surgical site.

Other known types of splash shields include flared disc-shaped or cone-shaped splash shields, or truncated cone or cylindrical shaped splash shields. These types of shields are typically substantially rigid and are generally provided as separate items from the tips, each including a hole at one end for attachment of a single shield to the distal end of a tubular lavage tip. These types of shields are typically relatively large shields, limiting their use and limiting visualization. These shields are also typically not designed to contact the working or surgical site.

Other examples of fluid delivery-type devices or instruments having a single flared shield member or the like are disclosed in the following U.S. Pat. Nos. 1,178,898 to Young; 1,602,215 to Smith; 1,889,425 to Sorensen; 2,771,072 to DeMontauge; 4,301,798 to Anderson and 4,465,479 to Meisch.

OBJECTS OF THE INVENTION

A principle object of this invention is to provide a lavage/suction tip which eliminates the problems of splashback and the possibility of cross contamination.

Another object of this invention is to provide a lavage/suction tip which includes a dual splash shield arrangement.

A further object of this invention is to provide such a lavage/suction tip having a dual splash shield which offers multiple options for surgical use providing an inner and an outer shield, where the outer shield is slidable along the barrel of the tip from a position of use over the inner shield to a position of non-use at a position spaced away from the inner distal shield.

A still further object of this invention is to provide such a lavage/suction tip having a dual splash shield wherein the outer shield is substantially rigid and the inner shield is pliable.

SUMMARY OF THE INVENTION

The present invention provides a lavage/suction tip which includes an elongated barrel providing a first fluid delivery passageway therein. The barrel includes a first shield extending outwardly from the distal tip of the first barrel. The tip further includes a second shield extending outwardly from the first barrel. The second shield is preferably slidable along the first barrel enabling the second shield to be selectively positioned at a plurality of locations along the first barrel.

The first shield is preferably pliable, while the second shield is preferably substantially rigid. Both shields may conveniently be conically flared with the larger end of the cone distal to the narrower end of the cone. The second shield may be positioned to substantially surround the first cone to provide the shield assembly with firm support, and yet with a flexible tip perimeter. The most distal end of the flared first shield preferably would still extend beyond the most distal end of the flared second shield which surrounds it. Alternatively, the second shield may be positioned and secured on the tip spaced away from the first shield so that the pliable first shield is used alone. When used alone, the first pliable shield may be easily, manually formed to more closely match the tip of the first shield to the working area of the surgical site.

BRIEF DESCRIPTION OF THE DRAWINGS

These features and objects of the invention as well as others, will become apparent to those skilled in the art by referring to the accompanying drawings in which.

DETAILED DESCRIPTION OF THE INVENTION

Figure 1:
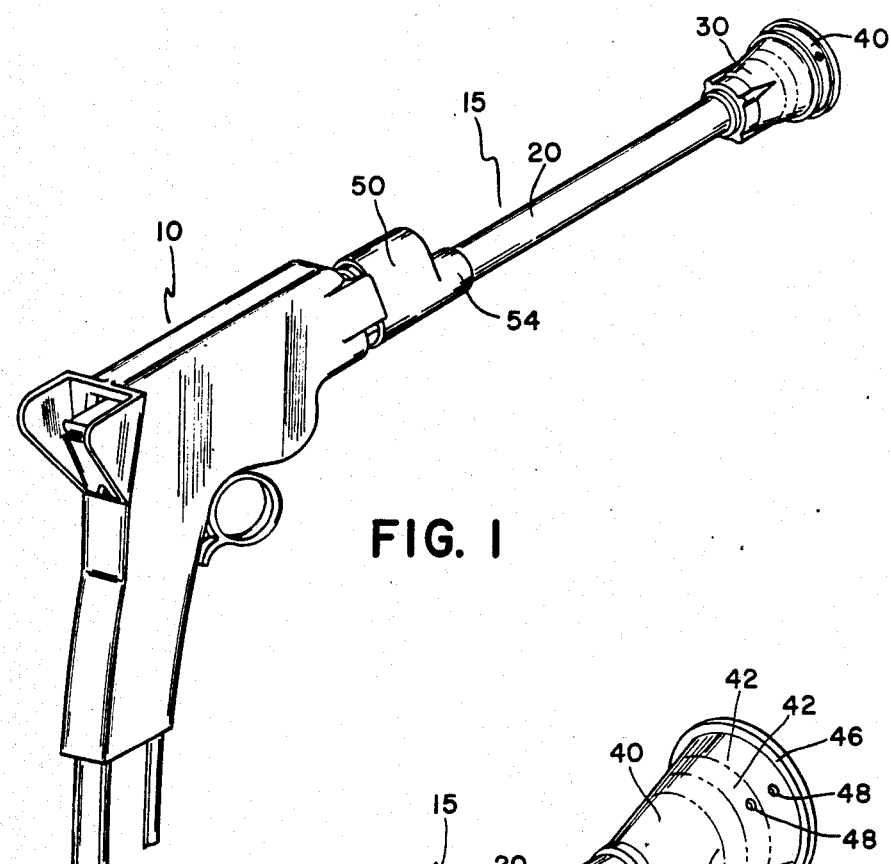
FIG. 1 is a perspective view of a lavage/suction tip according to the present invention illustrated in connection with a suitable lavage/suction handpiece.
Figure 2:
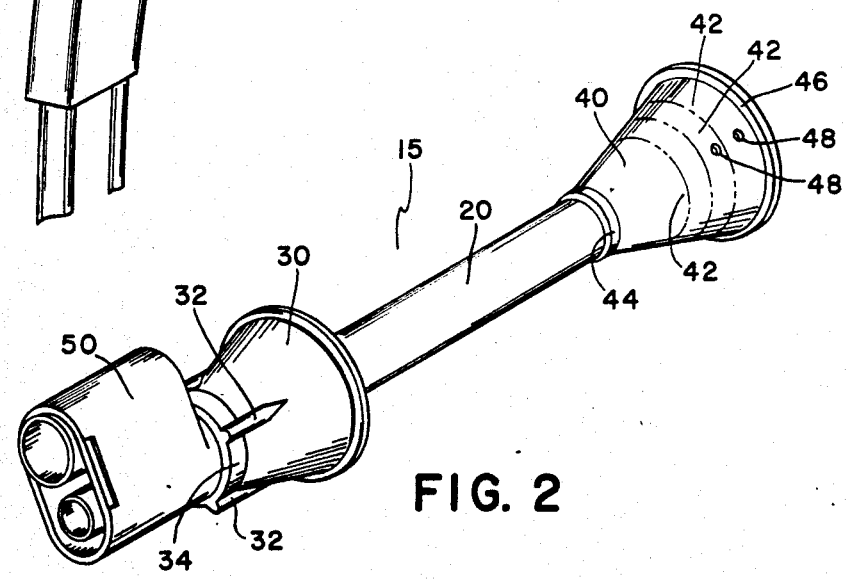
FIG. 2 is a perspective view of the lavage/suction tip of FIG. 1.
Figure 3:
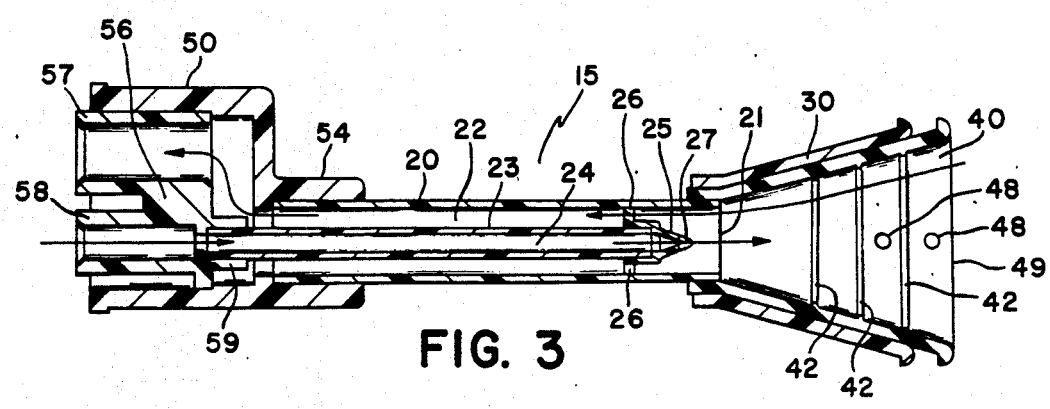
FIG. 3 is a cross-sectional side view of the lavage/suction tip of FIG. 1.

FIGS. 1-3 illustrate a particularly advantageous embodiment of the lavage/suction tip according to this invention. It is noted that in the embodiment illustrated, the lavage/suction tip 15 is shown as a separate unit attached to a suitable lavage/suction handpiece 10 in FIG. 1. However, it is pointed out that the tip 15 could be integrally formed as part of such a handpiece 10, if desirable.

The lavage/suction tip 15 includes a first elongated barrel 20, providing a first fluid passageway 22 therein. A second elongated barrel 23 is centrally located within the first passageway 22 as shown in FIG. 3. The first passageway 22 is thus provided between the inner and outer barrels 23 and 20. A second fluid passageway 24 is provided within the second barrel 23. The first outer passageway 22 provides fluid communication between the lavage/suction tip 15 and a suction source (not shown) for drawing fluids and other materials away from the surgical site. The second inner passageway provides fluid communication between the lavage/suction tip 15 and an irrigant liquid source (not shown) for supplying irrigant liquid to the surgical site.

The tip 15 includes an adaptor housing 50 and a dual female adaptor 56 at its proximal end for connection of the tip 15 to a suitable handpiece 10. The female adaptor 56 is supported within the housing 50 and includes two female connectors 57 and 58 for attachment of the tip 15 to corresponding male connectors (not shown) on the handpiece 10. Connector 57 provides for fluid communication between the outer passageway 22, and the suction source, while connector 58 provides for fluid communication between the inner passageway 24 and the irrigant liquid source.

The second barrel 23 is supported within the first barrel 20 by support member 59, part of the adaptor 56, at the proximal end of barrel 23 and is supported by pegs 26 at the distal end of second barrel 23. Barrel 23 terminates at its distal end with a narrowed cone-shaped nozzle 25 having an opening 27 at the very end for discharge of the irrigation liquid. FIG. 3 illustrates two pegs 26 extending between the nozzle 25 and the inner wall of barrel 20. It is noted that these pegs 26 are slender spoke-like pegs and extend outwardly from the nozzle 25 at approximately 180° from each other leaving substantial radial space between the pegs such that fluid communication is still provided between passageway 22 and the distal open end 21 of barrel 20. The nozzle 25 terminates proximally to the distal open end 21 of barrel 20. The nozzle 25 may be bonded or otherwise secured to the distal end of the second barrel 23.

The proximal end of barrel 20 extends into the adaptor housing 50. A collar 54 extends from the housing 50 and surrounds the proximal end of barrel 20. The proximal end of the barrel 20 may be secured to the housing 50 by a suitable bonding material. The dual female adaptor 56 within the adaptor housing 50 may also be bonded to the respective mating portions of the housing 50 and the inner second barrel 23. It is understood that any suitable means of connecting or securing the components may be utilized.

The lavage/suction tip 15 includes a dual splash shield arrangement, includiing a first inner shield 40 and a second outer shield 30.

The first inner shield 40 extends outwardly from the distal end of the first barrel 20. The first shield 40 includes a ring portion 44 surrounding the distal end of barrel 20. The first shield 40 conically flares outwardly from the ring 44, tapering distally outward from the first barrel 20. The first shield may be secured to the barrel 20 by use of a bonding material, although other suitable means of securing the components may be utilized.

The first shield 40 is preferably made from a pliable material, enabling it to be flexible and easily shaped. Such a suitable material is polyvinyl chloride, although any suitable pliable material may be utilized.

The second outer shield 30 also extends outwardly from first barrel 20 and is adapted to fit about the first shield 40. The second shield 30 is slidable along barrel 20. the second shield 30 has a ring portion 34 which encircles the first barrel 20 and which has an inner diameter larger than the outer diameter of the first barrel 20 to enable sliding readily therealong. The second shield 30 conically flares outwardly from the ring 34, tapering distally outward from the first barrel 20. The second shield 30 is preferably substantially rigid and may be conveniently made from acrylic, as may the barrels and adaptor components, although any suitable material may be utilized. Both shields 30 and 40 are preferably transparent for user convenience to improve visualization.

The second shield 30 may be selectively located at a plurality of positions along the first barrel 20. The second shield 30 is shown located in a first position in FIGS. 1 and 3, and a second position in FIG. 2. In FIGS. 1 and 3, the second outer shield 30 is at a first position substantially surrounding the first inner shield 40. The second shield 30 preferably does not completely encompass the first shield 40, leaving the distal peripheral edge of the first shield 40 exposed. The ring 34 of the second shield 30 fits securely about the ring 44 of the first shield 40 which is raised from the first barrel 20. The second shield 30 may readily be secured in this first position by a tapered friction fit between the conical shapes of shields 30 and 40. When the second shield 30 is in this first position about the first shield 40, the second substantially rigid shield 30 provides firm support about the first pliable shield with a flexible tip perimeter.

The distal open end 21 of barrel 20 communicated with the internal chamber of the first splash shield 40 which is open at its distal end 49. For example, when utilizing the lavage/suction tip 15 to provide debriding action to clean out bone surfaces such as during joint replacement surgery, the irrigation liquid exits from the irrigation outlet 27. This action against the surgical site creates a lot of splashing of the irrigant liquid. With the flared splash shields 40 and 30 extending outwardly from the distal tip of barrel 20, the distal rim 46 of the shield 40 may be placed directly on the bone/tissue surface such as a tibial plateau or an acetabular surface, and the splash will be contained within the shield 40. The simultaneous suction provided through passageway 22 draws the fluid back through the tip 15 along with any other liquids and any debris which has been loosened by the debridement at the surgical site. The suction removes any fluid and debris from the site through the suction passageway 22 and through the handgun 10 to collection suction cannisters (not shown). Containment within the shield 40 eliminates the messy splashing which would otherwise occur. With the firm outer second shield 30 in place about the inner pliable shield 40 as shown in FIGS. 1 and 3, the pliable shield 40 will stay round allowing the operator to clean all the area under the shield.

Alternatively, the second shield 30 may be selectively located in a second position along the barrel 20 proximally away from the first shield 40, as shown in FIG. 2. The second shield 30 may be conveniently secured in this second position by friction fit of the second shield ring 34 on or about the adaptor collar 54. With the outer second shield 30 back on this second position, the operator can shape the soft, inner first shield 40 to the area to be cleaned. When the first shield 40 is used alone, the pliable shield 40 is easily formed by the thumb and index finger of the operator to more closely conform or match the tip to the working area/surface.

To separate the second shield 30 from either the secured first position about neck 44 of the first shield 40 or from the secured second position at the adaptor collar 54, the operator grasps the firm outer shield and applies a twisting and pulling motion thereto to loosen the friction fit securement. A gripping means such as the plurality of protruding ribs 32 on the outer second shield 30 may be provided to aid in twisting and loosening the second shield 30 from either of its secured positions. The second shield 30 is manually grasped to selectively slide it along barrel 20 from one position to another.

The first shield 40 may also include one or more vacuum break holes 48. In the embodiment shown, first shield 40 includes two such holes 48. When the first shield 40 is used alone as in FIG. 2, both break holes 48 are exposed. Covering either or both of these with the fingers of the operator will increase the suction pressure. When the second shield 30 is secured about the first shield 40, the second shield 30 may be of such length that one of the two holes 48 is covered and one is not. This still provides for the operator to selectively close or open that one vacuum break hole to control the suction pressure.

In addition, the inner, pliable first shield 40 may include annular ring guides 42. The tip size of the pliable shield 40 can be selectively reduced by cutting along the annular ring guides. By cutting down the soft first shield 40, the operator is able to get into tighter spaces and still have splash shield protection.

It is noted that the second shield 30 may be positioned about the first shield 40, as shown in FIGS. 1 and 3, to provide support for shield 40 during its packaged life, preventing collapse of shield 40 during sterilization and storage.

It is also noted that the individual components of the tip 15 may be readily molded. The components are then assembled and secured together accordingly. However, any suitable manufacturing technique may be used for this tip 15. Typical dimensions for the tip 15 may provide the first outer barrel 20 with a length up to 20 inches, although 6 to 8 inches is generally a particularly convenient length. The outer diameter of the outer barrel 20 may typically be ½ inch, while the second inner barrel 23 may have a typical outer diameter of 3/16 inch. The thickness of barrels 20 and 23 may be approximately 1/32 inch. The first and second sheilds 40 and 30 may have approximate lengths of 1½ inches and 1⅛ inches, respectively. The inner diameter of the distal open end of first shield 40 may be approximately 1¼ inches. The shields are preferably sized to provide good visualization at the surgical site. The shields 40 and 30 taper at an angle of about 30 degrees. It is noted, however, that any suitable dimensioning may be provided to fit the needs of the operator.

The invention described herein is a lavage/suction tip which incorporates a dual splash shield arrangement. While this invention has been described and exemplified in terms of a particularly advantageous embodiment, those skilled in the art can appreciate that modifications can be made without departing from the spirit and scope of this invention.

What is claimed is:

1. A lavage/suction tip or the like comprising:
   a first elongated barrel including a distal tip and a proximal end, the first barrel having a first fluid passageway therein extending from one end to the other end;
   a first shield connected to the first barrel and extending radially and distally outwardly from the distal tip of the first barrel defining an expanded state of the first shield; and
   a second shield located about the first barrel and extending outwardly from the first barrel and adapted to fit about the first shield when the first shield is in said expanded state, and wherein the first shield has a first end and a second end connected therebetween by a wall member, wherein the first end is connected to the distal tip of the first barrel and the second end extends in a direction away from the distal tip and opposite the proximal end, the wall member forms an enlarged chamber therewithin which is in fluid communication with the first passageway, the chamber being open at its second end.

2. The lavage/suction tip of claim 1 wherein the second shield is slidable along the first barrel, enabling the second shield to be selectively positioned at a plurality of locations along the first barrel.

3. The lavage/suction tip of claim 1 wherein the first shield is pliable and the second shield is substantially rigid.

4. The lavage/suction tip of claim 3 wherein said tip includes a first securing position toward the distal tip of the first barrel at which the second shield may be selectively positioned and secured to substantially surround the first shield to provide firm support about the first pliable shield, and said tip includes a second securing position spaced away from the distal tip of the first barrel at which the second shield may alternatively be selectively positioned and secured to provide a position of non-use for the second shield along the barrel away from the first shield.

5. The lavage/suction tip of claim 4 wherein the tip includes an adaptor housing at the proximal end of the first barrel to connect the tip to a suitable lavage/suction handpiece and wherein the adaptor includes a collar which extends about the first barrel such that the second shield may be selectively positioned in the second position by sliding the second shield onto the collar to frictionally secure the second shield in the second position.

6. The lavage/suction tip of claim 4 wherein the second shield is frictionally secured at either its first position or its second position, and wherein the second shield includes a gripping means to enable the second shield to be twisted to loosen the second shield from either of its secured positions.

7. The lavage/suction tip of claim 6 wherein the gripping means includes a plurality of protruding ribs.

8. The lavage/suction tip of claim 4 wherein the first shield forms a wall and includes at least one hole therethrough the wall of the first shield, and wherein said at least one hole may be selectively covered to increase the suction pressure.

9. The lavage/suction tip of claim 4 wherein the first and second shield each include a peripheral rim, respectively, and the peripheral rim of the first pliable shield extends beyond the peripheral rim of the substantially rigid second shield when the second shield is in the first position.

10. A lavage/suction tip or the like comprising:
    a first elongated barrel including a distal tip and a proximal end, the first barrel having a first fluid passageway therein extending from one end to the other end;
    a first elongated shield connected to the first barrel and extending outwardly from the distal tip of the first barrel; and
    a second shield located about the first barrel and extending outwardly from the first barrel and adapted to fit about the first shield and wherein the first shield has a first end and a second end connected therebetween by a wall member, wherein the first end is connected to the distal tip of the first barrel and the second end extends in a direction away from the distal tip and opposite the proximal end, the wall member forms an enlarged chamber therewithin which is in fluid communication with the first passageway, the chamber being open at its second end, wherein the first and second shields are both conically flared, tapering distally outwardly from the first barrel.

11. A lavage/suction tip or the like comprising:
a first elongated barrel including a distal tip and a proximal end, the first barrel having a first fluid passageway therein extending from one end to the other end;
a first shield connected to the first barrel and extending outwardly from the distal tip of the first barrel; and
a second shield located about the first barrel and extending outwardly from the first barrel and adapted to fit about the first shield and wherein the first shield has a first end and a second end connected therebetween by a wall member, wherein the first end is connected to the distal tip of the first barrel and the second end extends in a direction away from the distal tip and opposite the proximal end, the wall member forms an enlarged chamber therewithin which is in fluid communication with the first passageway, the chamber being open at its second end, wherein said tip is for use at a surgical site, wherein the first elongated barrel includes a second elongated barrel supported within the passageway of the first barrel providing the first fluid passageway as an outer passageway between the first and second barrels for connection to a suction source for drawing fluids and other materials away from the surgical site and providing a second inner fluid passageway within the second barrel for connection to an irrigant liquid source for supplying irrigant liquid to the surgical site.

12. A lavage/suction tip or the like comprising:
a first elongated barrel including a distal tip and a proximal end, the first barrel having a first fluid passageway therein extending from one end to the other end;
a first shield connected to the first barrel and extending outwardly from the distal tip of the first barrel; and
a second shield located about the first barrel and extending outwardly from the first barrel and adapted to fit about the first shield and wherein the first shield has a first end and a second end connected therebetween by a wall member, wherein the first end is connected to the distal tip of the first barrel and the second end extends in a direction away from the distal tip and opposite the proximal end, the wall member forms an enlarged chamber therewithin which is in fluid communication with the first passageway, the chamber being open at its second end, wherein the first shield is pliable and the second shield is substantially rigid, wherein the first pliable shield includes a plurality of spaced annular ring guides to provide a guide for cutting the first shield down in length.

13. A lavage/suction tip of the like comprising:
a first elongated barrel including a distal tip and a proximal end, the first barrel having a first fluid passageway therein extending from one end to the other end;
a first shield connected to the first barrel and extending outwardly from the distal tip of the first barrel; and
a second shield located about the first barrel and extending outwardly from the first barrel and adapted to fit about the first shield and wherein the first shield has a first end and a second end connected therebetween by a wall member, wherein the first end in connected to the distal tip of the first barrel and the second end extends in a direction away from the distal tip and opposite the proximal end, the wall member forms an enlarged chamber therewithin which is in fluid communication with the first passageway, the chamber being open at its second end and wherein the first shield is pliable and the second shield is substantially rigid, and wherein said tip includes a first securing position toward the distal tip of the first barrel at which the second shield may be selectively positioned and secured to substantially surround the first shield to provide firm support about the first pliable shield, and said tip includes a second securing position spaced away from the distal tip of the first barrel at which the second shield may alternatively be selectively positioned and secured to provide a position of non-use for the second shield along the barrel away from the first shield, and wherein the first shield forms a wall and includes at least one hole therethrough the wall of the first shield, and wherein said at least one hole may be selectively covered to increase the suction pressure, and wherein the first shield includes two spaced holes and wherein when the second shield is in the first position about the first shield, the second shield covers one of the holes and leaves the other exposed to enable the exposed hole to be selectively covered to increase the suction pressure.

14. A lavage/suction tip of the like comprising:
an outer elongated barrel including a distal tip and a proximal end, the outer barrel having a first fluid passageway therein;
a first pliable shield connected to the outer barrel and extending from the distal tip of the outer barrel; and
a means for reinforcing the first pliable shield, said means providing such reinforcing without substantially deforming the first shield, and wherein said tip is for use at a surgical site, wherein the outer elongated barrel includes an inner elongated barrel supported within the passageway of the outer barrel providing the first fluid passageway as an outer passageway between the outer and inner barrels for connection to a suction source for drawing fluids and other materials away from the surgical site and providing a second inner fluid passageway within the second barrel for connection to an irrigant liquid source for supplying irrigant liquid to the surgical site.

15. The lavage/suction tip of claim 14 wherein said means is a second rigid shield located about the first barrel and adapted to fit about the first shield, wherein the second shield may be selectively utilized to be operative in effecting reinforcement of the first shield or to be non-operative, thus not providing such reinforcement.

16. A lavage/suction tip or the like comprising:
a first elongated barrel including a distal tip and a proximal end, the first barrel having a first fluid passageway therein;
a first pliable shield connected to the first barrel and extending radially and distally outwardly from the distal tip of the first barrel defining an expanded state of the first shield; and a means for reinforcing the first pliable shield, wherein said means may be selectively utilized to be operative in effecting reinforcement of the first shield or to be non-operative, thus not providing such reinforcement, and wherein said means is a substantially rigid second shield located about the first barrel and extending outwardly from the first barrel and adapted to fit about the first shield when the first shield is in said expanded state, to selectively provide reinforcement of the first shield.

17. A lavage/suction tip or the like comprising:

an outer elongated barrel including a distal tip and a proximal end, the outer barrel having a first fluid passageway therein;

a first shield connected to the outer barrel and extending from the distal tip of the outer barrel for operating in a predetermined manner with predetermined operating characteristics; and a means for selectively cooperating with the first shield to alter the operating characteristics of the first shield without substantially deforming the first shield, and wherein said tip is for use at a surgical site, wherein the outer elongated barrel includes an inner elongated barrel supported within the passageway of the outer barrel providing the first fluid passageway as an outer passageway between the outer and inner barrels for connection to a suction source for drawing fluids and other materials away from the surgical site and providing a second inner fluid passageway within the second barrel for connection to an irrigant liquid source for supplying irrigant liquid to the surgical site.

* * * * *